United States Patent [19]

Schmid, Jr. et al.

[11] 4,433,779
[45] Feb. 28, 1984

[54] DENTIST'S APPARATUS FOR STORING AND VIBRATION MIXING OF AMALGAM COMPONENTS

[75] Inventors: Alfred Schmid, Jr.; Hans Müller; Alexander P. Jaecklin, all of St. Gall, Switzerland

[73] Assignee: Coltene AG, Switzerland

[21] Appl. No.: 457,159

[22] Filed: Jan. 11, 1983

[30] Foreign Application Priority Data

Jan. 19, 1982 [CH] Switzerland .......................... 304/82

[51] Int. Cl.³ .......................................... B65D 25/08
[52] U.S. Cl. .................................. 206/220; 206/63.5; 241/199; 366/602
[58] Field of Search ....................... 206/63.5, 219, 220, 206/221, 222, 568, 216; 215/6, DIG. 8; 241/199, 199.6, 199.9, 291; 366/602

[56] References Cited

U.S. PATENT DOCUMENTS 2,642,065  6/1953  Negri ................................... 206/222
2,892,595  6/1959  Tupper ................................ 241/199
2,935,189  5/1960  Barton ................................ 206/568
4,134,494  1/1979  Wong .................................. 206/216

FOREIGN PATENT DOCUMENTS 924663  5/1963  United Kingdom .................... 215/6

Primary Examiner—George E. Lowrance
Assistant Examiner—Jimmy G. Foster
Attorney, Agent, or Firm—Burns, Doane, Swecker & Mathis

[57] ABSTRACT

The present invention relates to a capsule for storing and vibration mixing of two component materials for dental application, particularly of dental amalgam components. The capsule encloses a mixing space in which a first component and a pestle are disposed. The pestle is in the form of a hollow body with a removable cover. The pestle serves as a container for a second component and has at least one opening. The opening permits the exit of the second component which opening is rendered passable as a result of a mixing vibration movement.

18 Claims, 9 Drawing Figures

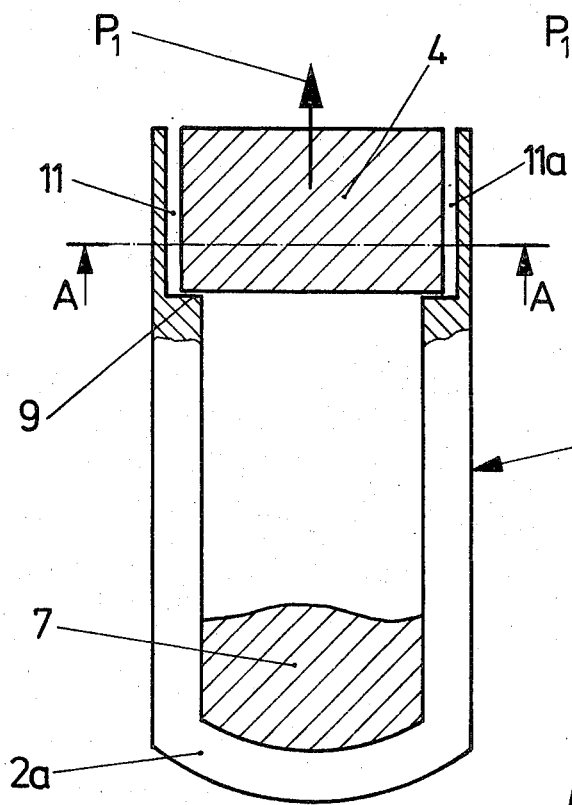
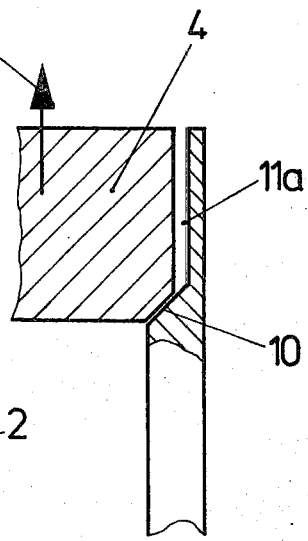
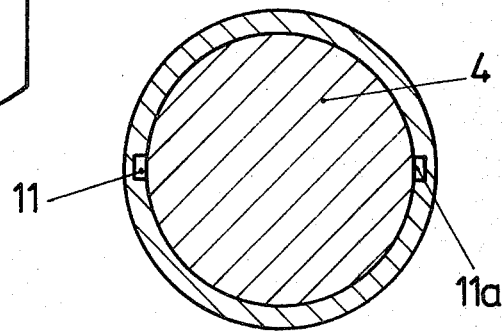
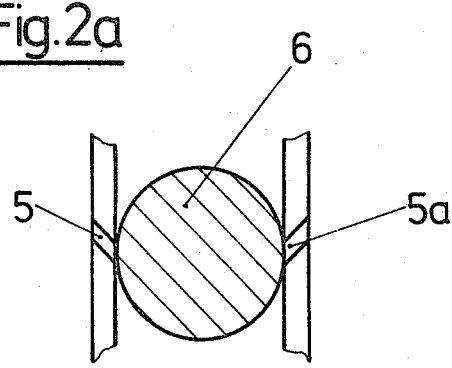
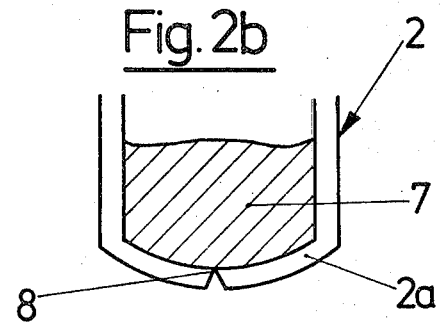

DENTIST'S APPARATUS FOR STORING AND VIBRATION MIXING OF AMALGAM COMPONENTS

BACKGROUND AND SUMMARY OF THE PRESENT INVENTION

The present invention relates to a capsule for storing and vibration mixing of two component materials for dental application, particularly of amalgam components.

A known capsule for separate storage and vibration mixing of amalgam components (U.S. Pat. No. 3,139,181) has a generally cylindrical lower capsule part containing the mixing space, and an upper part for storing the first component. The second component is disposed in the mixing space along with a pestle. Immediately before the mixing of the components the first component is introduced into the mixing space by a screwing movement exerted on the upper capsule part. Then the capsule is inserted in the vibration mixer which causes the capsule to move back and forth at a high frequency in the longitudinal direction, whereby the second component forms a homogeneous mixture with the first component. A disadvantage of this known multicomponent capsule is that a specific manipulatory movement must be executed before the mixing process in order to transfer the first component into the mixing space.

In another known arrangement (Ger. Pat. App. No. 28 31 005), one of the two components to be mixed is stored packaged in a foil or film bag in the mixing space, while the other component is stored open in the space. When the mixing vibration starts, it causes the foil or film bag to break, thus liberating the component stored therein to be mixed with the other component. This arrangement has the advantage that no specific manipulation is required to transfer the first component into the mixing space. However, there are problems associated with packaging the component in the foil or film bag. In particular, it is virtually impossible to weld-seal the bag so as to leave a consistent, small free volume above the component. This variation in free volume has a major effect on the time at which the bag breaks after the onset of the vibration action. Accordingly, it is difficult to achieve consistently good mixing given a prescribed mixing time. Also, there is the possibility that part of the broken bag will end up in the final amalgam and contaminate it.

A similar arrangement has been proposed (Ger. Pat. App. No. 30 25 526) in which the two components in the capsule are separated by a wall which divides the mixing space into two compartments and which has a bonding locus near its junction with the interior surface of the mixing space. The bonding locus is caused to break under the influence of the mixing vibration. The separating wall is preferably of a soft elastic material such as silicone rubber. However, this capsule also has the disadvantage that it is difficult to control sufficiently accurately the time at which the bonding locus of the separating wall will open or break.

The two last-mentioned capsules additionally have the disadvantage that a pestle cannot be used with them, and therefore the second component may be employed only in powder form and not in tablet form. In dental amalgams, where the first component is comprised of mercury and the second is comprised of a silver alloy, it is very advantageous for the latter to be employable in table form, to facilitate the control of the quantity employed.

Accordingly, it is an object of the present invention to devise a capsule for the storing and vibration mixing of dental two component materials, particularly of dental amalgam components, whereby the above-mentioned disadvantages of the known capsules can be avoided.

This object and other are achieved by a capsule for storing and vibration mixing of amalgam components or other two component materials for dental application according to the present invention. The capsule includes a mixing space which contains a first component and a pestle. The pestle is a hollow body containing a second component. The hollow body has a cover secured thereto and includes at least one opening for permitting the exit of the second component. The second component is rendered capable of passing through the opening by a mixing vibration movement of the body.

The inventive capsule has the advantages, first, that no special manipulation is required to transfer the one component into the mixing space prior to mixing the components, and secondly, a pestle is employed, thus permitting the other component to be used in tablet form. Since the mixing of the components is associated with substantial evolution of heat as a result of internal friction, a pestle with a metal cover may be used to facilitate heat removal. The metal cover also affords higher weight, which is beneficial for comminuting the tablets. The double containment within the pestle and the capsule provided for the mercury in the pestle is well suited for storing the mercury, and provides good oxidation protection. Further, in case of a defect in the seal of the pestle, the mercury is retained in the plastic capsule and cannot cause external pollution during shipping or storage.

BRIEF DESCRIPTION OF THE DRAWINGS

Preferred embodiments of the present invention will be described in greater detail hereinafter, with reference to the accompanying drawings, wherein like members bear like reference numerals and wherein:

FIG. 2a is a partial view of a variant of the pestle of FIG. 2;

FIG. 2b is a partial view of a second variant of the pestle of FIG. 2, corresponding to the view shown in FIG. 2;

FIG. 3 is a central longitudinal cross sectional view of a second pestle embodiment;

FIG. 3a is a cross section through line A—A in FIG. 3;

FIG. 3b is a partial view of a variant of the pestle embodiment of FIG. 3;

DETAILED DESCRIPTION OF THE PREFERRED EMBODIMENTS

Figure 1:
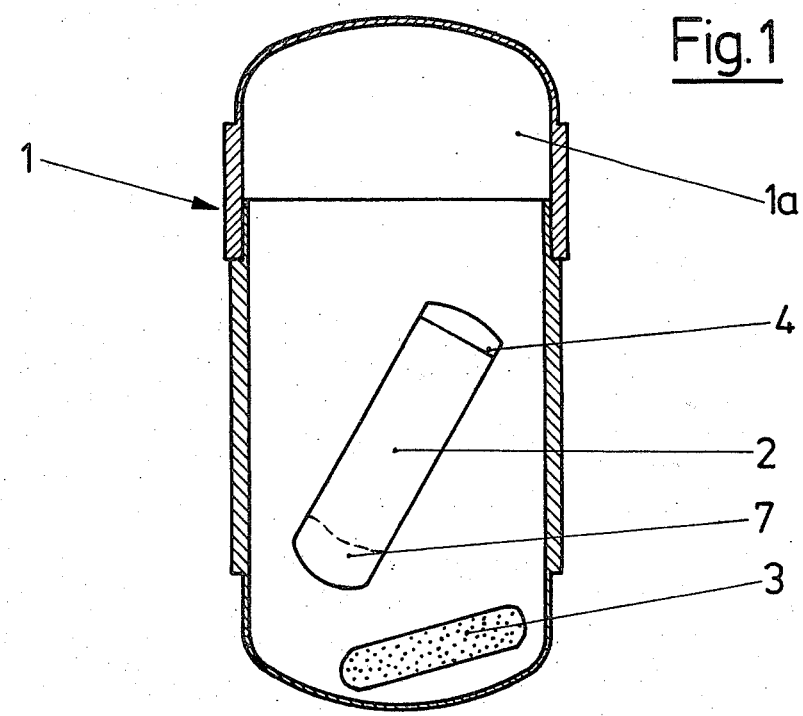
FIG. 1 is a central longitudinal cross sectional view of the inventive capsule.

The inventive capsule comprises an ordinary, cylindrical, sealable, plastic capsule 1 (FIG. 1) with a cap 1a.

The interior cavity of the capsule comprises the mixing space, wherein a hollow pestle 2 and one of the components of the amalgam in the form of a tablet 3 are disposed. A powder could be provided in place of the tablet 3, if desired.

Figure 2:
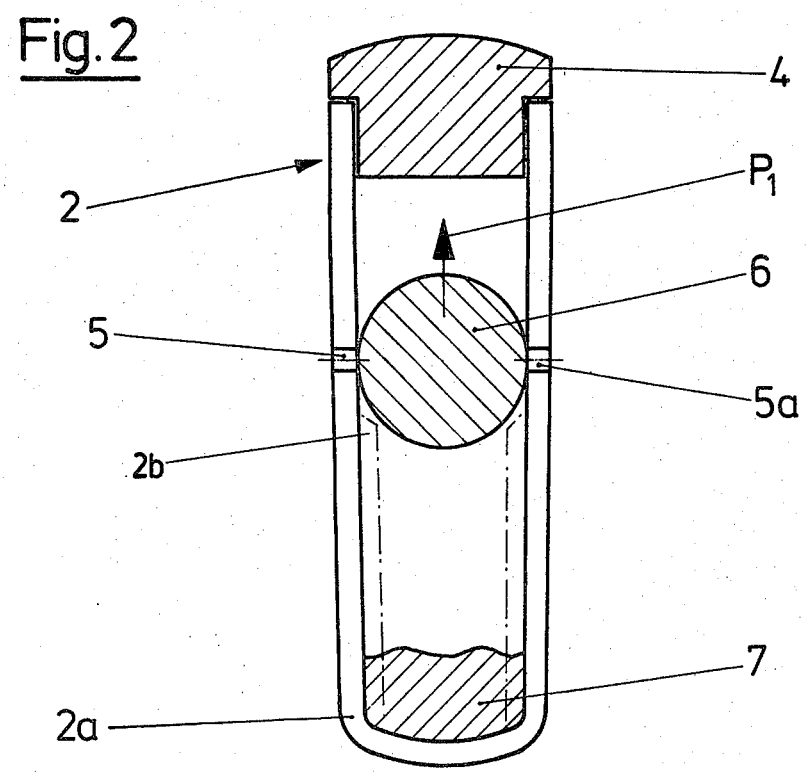
FIG. 2 is an enlarged central longitudinal cross sectional view of the pestle.

With reference to FIG. 2, the pestle 2 comprises a generally cylindrical hollow body which narrows to a slight degree in conical fashion in the direction toward its bottom 2a. Instead, the hollow body 2 could also be straight cylindrical, a step 2b being provided on its interior surface as indicated in broken lines. The bottom 2a is curved in the manner of a lens. The pestle 2 is of a plastic material such as polyethylene, polypropylene, polystyrene or some other polymer. A cover 4, also curved in lens-shaped fashion, fits telescopically into the open end of the hollow body 2. The cover 4 is of metal, preferably stainless steel, or may also be of a plastic material. There are one or more openings 5, 5a in the cylindrical wall of the pestle 2, which openings are closed off when in the rest state by a sealing element 6 such as a spherical plug made of an elastic material, e.g., rubber. Alternatively, the plug 6 may have a disc shape.

In charging the pestle 2, mercury 7 is charged first, then the plug 6 is pushed in, and finally the cover 4 is applied.

In operation the pestle 2 and the tablet 3 are inserted in the capsule 1, and the capsule is subjected to the action of any commercially available vibration mixer. The vibrating action causes the pestle 2 to move back and forth in its longitudinal direction and collide with the walls of the capsule. In the process, the plug 6 is moved in the direction of the arrow $P_1$, thus exposing the openings 5 and 5a, whereby the mercury exits into the interior free space of the capsule 1. At the same time the pestle 2 acts to comminute the tablet 3 thereby breaking up the silver alloy contained in the tablet, which is then homogeneously mixed with the mercury.

In the embodiment of FIG. 2a, the openings 5 and 5a in the cylindrical wall run at an acute angle to the axis of the pestle, thus facilitating the exit of the mercury.

In a second embodiment (FIG. 2b), there is a prearranged locus of breakage 8 in the form of a groove or scoring, in the form of a line or cross, in the bottom 2a of the pestle 2. Under the influence of the vibrating motion, the locus of breakage gives way, permitting the mercury to exit.

In the embodiment of the pestle according to FIGS. 3 and 3a, the cover 4 inserted in the open end of the hollow body is flat on its upper end, and the interior side of the wall of the hollow body of the pestle 2 has two channel-shaped openings 11 and 11a in the side wall which openings run parallel to the axis of the pestle. In the rest state the cover 4 rests against a horizontal seal 9. Under the influence of the vibrating motion the cover 4 readily moves in the direction of arrow $P_1$, enabling the mercury to exit through the openings 11 and 11a.

In the embodiment of FIG. 3b, the lower end of the cover 4 has a truncated conical shape and rests on a seal 10 which is also conical. This arrangement facilitates the exit of the mercury.

Figure 4:
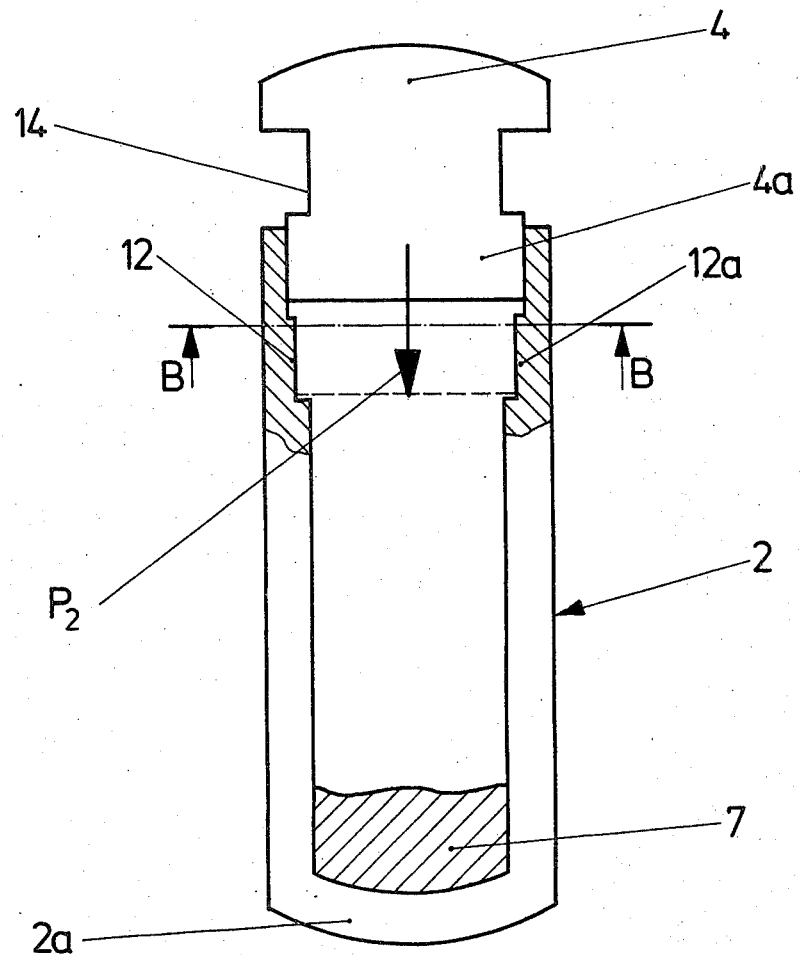
FIG. 4 is a central longitudinal cross sectional view of a third pestle embodiment.
Figure 4A:
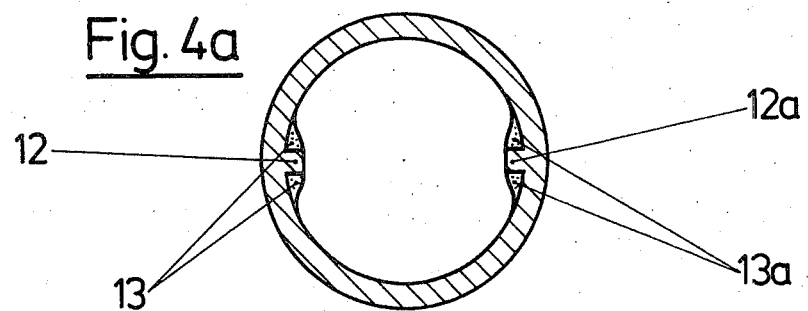
FIG. 4a is a cross section through line B—B in FIG. 4.

In a further embodiment of the pestle 2 (FIGS. 4 and 4a), the open end of the hollow body has two diametrically opposite longitudinal ridges 12 and 12a of rectangular cross section, on its internal wall. The cover 4 is of an elastic material such as rubber and has a neck section 14 in its middle region. Under the influence of the vibration motion, a portion 4a of the cover 4 is pushed into the open end of the hollow body, in the direction of arrow $P_2$, to the extent that it undergoes compression and pinching by the longitudinal ridges 12 and 12a, as seen from FIG. 4a. This compression forms openings 13 and 13a through which the mercury can move out into the region of the neck 14 and from there into the mixing space.

The cover 4 may alternatively be of a solid material, such as metal, instead of being wholly or partially of an elastic rubberoid material. In such a case, the portion 4a will be provided with an annular groove containing an O-ring of an elastic rubberoid material, which O-ring undergoes pinching by the longitudinal ridges 12 and 12a.

The capsules according to the invention, as described with reference to the drawings, are particularly advantageous for storing amalgam components for dental application. However, the capsules could also be used, with similar advantages, for other two component dental materials, for example cements, in which case one component could be a calcium hydroxide or phosphate cement powder or tablet, and the other component a suitable liquid.

The principles, preferred embodiments and mode of operation of the present invention have been described in the foregoing specification. However, the invention which is intended to be protected is not to be construed as limited to the particular embodiments disclosed. The embodiments are to be regarded as illustrative rather than restrictive. Variations and changes may be made by others without departing from the spirit of the present invention. Accordingly, it is expressly intended that all such variations and changes which fall within the spirit and scope of the present invention as defined in claims be embraced thereby.

What is claimed is:

1. A capsule for storing and vibration mixing of two component materials for dental application, comprising a mixing space which contains a first component and a pestle, the pestle being in the form of a hollow body which contains a second component, the hollow body being provided with a cover which is attached to the hollow body, the pestle includes at least one opening which permits exit of said second component into the mixing space, and said opening being rendered passable as a result of a mixing vibration movement.

2. A capsule according to claim 1, wherein said two components are dental amalgam components.

3. A capsule according to claim 1, wherein the pestle is generally cylindrical in shape.

4. A capsule according to claim 3, wherein the pestle comprises a hollow body which narrows in a conical fashion in the direction toward its bottom.

5. A capsule according to claim 3, wherein the pestle is cylindrical and includes a step formed in the interior surface of its wall.

6. A capsule according to claim 3, wherein the at least one opening in the pestle runs perpendicular to the axis of said pestle.

7. A capsule according to claim 3, wherein the at least one opening in the pestle runs at an acute angle to the axis of said pestle.

8. A capsule according to claim 3, wherein the at least one opening runs parallel to the axis of said pestle.

9. A capsule according to claim 1, further comprising a seal for closing off the opening or openings in the rest state.

10. A capsule according to claim 9, wherein the seal which closes off the at least one opening is spherical.

11. A capsule according to claim 9, wherein the seal which closes off the at least one opening has a disc shape.

12. A capsule according to claim 9, wherein the seal is comprised of an elastic material.

13. A capsule according to claim 1, wherein the bottom and the cover of the pestle are curved in the fashion of a lens.

14. A capsule according to claim 1, wherein the hollow body of the pestle is of plastic, and the cover of the pestle is of metal.

15. A capsule according to claim 1, wherein the opening comprises a prearranged locus of breakage comprising a groove or scoring in the form of a line or cross in the bottom of the pestle.

16. A capsule according to claim 1, wherein the cover of the pestle rests against a seal, said cover being moved away from the seal under the influence of the mixing vibration motion such that at least one channel-shaped opening on the interior side of the wall of the hollow body is rendered passable.

17. A capsule according to claim 1, wherein at least a lower portion of the cover of the pestle is comprised of a rubberoid elastic material, said cover being pushed into the open end of the hollow body under the influence of the mixing vibration motion, such that the lower portion of the cover is compressed and pinched by at least one ridge provided on an interior side of the wall of the hollow body, said compression forming said openings.

18. A capsule according to claim 1, wherein the hollow body pestle is employed for a heavy liquid, particularly mercury.

* * * * *